(12) United States Patent
Singh (10) Patent No.: US 7,179,484 B2
(45) Date of Patent: Feb. 20, 2007

(54) PROTEIN-STABILIZED LIPOSOMAL FORMULATIONS OF PHARMACEUTICAL AGENTS

(75) Inventor: Chandra U. Singh, San Antonio, TX (US)

(73) Assignee: Azaya Therapeutics, Inc., San Antonio, TX (US)

( * ) Notice: Subject to any disclaimer, the term of this patent is extended or adjusted under 35 U.S.C. 154(b) by 168 days.

(21) Appl. No.: 10/703,187

(22) Filed: Nov. 6, 2003

(65) Prior Publication Data

US 2004/0247660 A1     Dec. 9, 2004

Related U.S. Application Data (60) Provisional application No. 60/424,230, filed on Nov. 6, 2002.

(51) Int. Cl.
    *A61K 9/127* (2006.01)
(52) U.S. Cl. .................................... 424/450
(58) Field of Classification Search ............... 424/450
    See application file for complete search history.

(56) References Cited

U.S. PATENT DOCUMENTS

| | | | |
|---|---|---|---|
| 4,182,330 A | 1/1980 | Michaels | 128/260 |
| 4,485,054 A | 11/1984 | Mezei et al. | 264/4.6 |
| 4,515,736 A | 5/1985 | Deamer | 264/4.3 |
| 4,687,661 A | 8/1987 | Kikuchi et al. | 424/38 |
| 4,731,210 A | 3/1988 | Weder et al. | 264/4.3 |
| 4,826,689 A | 5/1989 | Violanto | 424/489 |
| 4,873,035 A | 10/1989 | Wong | 264/4.6 |
| 5,178,875 A | 1/1993 | Lenk et al. | 424/450 |
| 5,185,154 A | 2/1993 | Lasic et al. | 424/450 |
| 5,230,899 A | 7/1993 | Park et al. | 424/450 |
| 5,260,065 A | 11/1993 | Mathur et al. | 424/450 |
| 5,277,914 A | 1/1994 | Szoka, Jr. | 424/450 |
| 5,422,120 A | 6/1995 | Kim | 424/450 |
| 5,549,910 A | 8/1996 | Szoka, Jr. | 424/450 |
| 5,567,433 A | 10/1996 | Collins | 424/450 |
| 5,589,189 A * | 12/1996 | Moynihan | 424/450 |
| 5,702,722 A | 12/1997 | Tournier et al. | 424/450 |
| 5,723,147 A | 3/1998 | Kim et al. | 424/450 |
| 5,753,262 A * | 5/1998 | Wyse et al. | 424/450 |
| 5,766,627 A | 6/1998 | Sankaram et al. | 424/450 |
| 5,916,596 A * | 6/1999 | Desai et al. | 424/450 |
| 5,993,850 A | 11/1999 | Sankaram et al. | 424/450 |
| 5,993,851 A | 11/1999 | Foldvari | 424/450 |
| 6,007,838 A | 12/1999 | Alving et al. | 424/450 |
| 6,071,534 A | 6/2000 | Kim et al. | 424/450 |

(Continued)

FOREIGN PATENT DOCUMENTS

WO    WO 90/03795    *    4/1990

(Continued)

OTHER PUBLICATIONS

Papahadjopoulos et al., "Sterically Stabilized Liposomes: Improvements in Pharmacokinetic and Antitumor Therapeutic efficacy," PNAS, vol. 88, pp. 11460-11464.*

(Continued)

*Primary Examiner*—Carlos A. Azpuru
(74) *Attorney, Agent, or Firm*—Fulbright & Jaworski LLP (57) ABSTRACT

The present invention relates to protein stabilized liposomes. Specifically, the present invention discloses compositions and methods for protein stabilized liposomes, the creation of protein stabilized liposomes, and the administration of protein stabilized liposomes.

30 Claims, 1 Drawing Sheet

Pentanoyl-deacetyl-Colchicine

U.S. PATENT DOCUMENTS

| | | | | |
|---|---|---|---|---|
| 6,106,858 | A | 8/2000 | Ye et al. | 424/450 |
| 6,132,766 | A | 10/2000 | Sankaram et al. | 424/450 |
| 6,221,401 | B1 | 4/2001 | Zasadzinski et al. | 424/490 |
| 6,277,413 | B1 * | 8/2001 | Sankaram | 424/501 |
| 6,306,433 | B1 * | 10/2001 | Andersson et al. | 424/450 |
| 6,355,267 | B1 | 3/2002 | Collins | 424/450 |
| 6,447,800 | B2 | 9/2002 | Hope | 424/450 |
| 6,497,895 | B2 | 12/2002 | Uhrich | 424/422 |
| 2002/0001613 | A1 | 1/2002 | Niemiec et al. | 424/450 |
| 2002/0028219 | A1 | 3/2002 | Smyth-Templeton et al. | 424/400 |
| 2002/0039596 | A1 | 4/2002 | Hartounian et al. | 424/450 |
| 2002/0061331 | A1 | 5/2002 | Zasadzinski et al. | 424/451 |
| 2002/0119188 | A1 | 8/2002 | Niemiec et al. | 424/450 |
| 2002/0122819 | A1 | 9/2002 | Smyth-Templeton et al. | 424/450 |
| 2002/0127272 | A1 * | 9/2002 | Huang et al. | 424/450 |
| 2002/0160039 | A1 | 10/2002 | Boni et al. | 424/450 |
| 2003/0044454 | A1 | 3/2003 | Fukui et al. | 424/450 |

OTHER PUBLICATIONS

Papahadjopoulos et al. "Sterically Stabilized Liposomes: Improvements in Pharmacokinetic and Antitumor Therapeutic efficacy," PNAS, vol. 88, pp. 11460-11464.*

Papahodjopoulos et al., "Sterically Stabilized Liposomes: Improvements in Pharmacokinetic and Antitumor Therapeutic efficacy," PNAS, vol. 88, pp. 11460-11464.*

Beugin et al., "New sterically stabilized vesicles based on nonionic surfactant cholesterol and poly(ethylene glycol) cholesterol conjugates," *Biophysical J.*, 74: 3198-3210, 1998.

Cabanes et al., "Enhancement of antitumor activity of polyethylene glycol coated liposomal doxorubicin with soluble and liposomal interleukin 2," *Clinical Cancer Research*, 5:687-693.

Drummond et al., "Optimizing liposomes for delivery of chemotherapeutic agents to solid tumors," *Pharmacol. Rev.*, 51(4):691-744, 1999.

Gabizon and Papahadjopoulos, "Liposome formulations with prolonged circulation time in blood and enhanced uptake by tumors," *Proc. Nat. Acad. Sci. USA*, 85: 6949-6953, 1988.

Lasic, Sterically stabilized liposomes: a hypothesis on the molecular origin of the extended circulation times, *Biochimica et Biophysica Acta*, 1070: 187-192, 1991.

Müller and Müller-Goymann, "Influence of temperature on the manufacturing of liposomes," *Arch. Pharm. Med. Chem.*, 334(Suppl. 2):79, 2001.

Papahadjopoulos et al.., "Sterically stabilized liposomes: Improvements in pharmacokinetics and antitumor therapeutic efficacy," *Proc. Nat. Acad. Sci. USA*, 88:11460-11464, 1991.

Woodle et al., "Versatility in lipid compositions showing prolonged circulation with stericallly stabilized liposomes," *Biochimica and Biophysica Acta*, 1105: 193-200, 1992.

Working et al., "Reduction of the cardiotoxicity of doxorubicin in rabbits and dogs by encapsulation in long-circulating pegylated liposomes," *J Pharmacol and Exper Ther*, 289(2):1128-1133, 1999.

Working et al., "Comparative target organ toxicity of free and liposome-encapsulated doxorubicin in rats," *Toxicologist*, 14:217, 1994.

Working et al., "Pharmacokinetics, biodistribution, and therapeutic efficacy of doxorubicin encapsulated in stealth liposomes (Doxil)," *Journal of Liposome Research*, 4(1):667-687, 1994.

* cited by examiner

FIG. 1

PROTEIN-STABILIZED LIPOSOMAL FORMULATIONS OF PHARMACEUTICAL AGENTS

The present application claims priority to U.S. provisional application Ser. No. 60/424,230, filed Nov. 6, 2002, the entire specification of which is incorporated herein by reference.

BACKGROUND OF THE INVENTION

1. Field of the Invention

The present invention relates generally to the fields of drug delivery. More particularly, it concerns methods for preparing and administering a protein-stabilized lipid formulation containing at least one pharmaceutical agent.

2. Description of Related Art

Liposomes are phospholipid vesicles, composed mainly of naturally occurring substances that are nontoxic and biodegradable (Lasic 1993). They are made up of at least one lipid bilayer membrane containing an entrapped aqueous internal compartment. When combined with water, phospholipids immediately form a sphere because one end of each molecule is water soluble, while the opposite end is water insoluble. Water-soluble medications added to the water are trapped inside the aggregation of the hydrophobic ends; fat-soluble medications are incorporated into the phospholipid layer.

Liposomes are particularly useful for drug delivery. Liposomes have been employed for a number of therapeutic applications, in particular, for delivering drugs to target cells following systemic administration (Drummond et al., 1999; Gibbson and Paphadjopoulos 1988; Lasic and Paphadjopoulos 1998; Olson et al., 1982; Rahman et al., 1982; Working et al., 1994a; Working et al., 1994b; Working et al., 1996; Working et al., 1999; Mayer et al., 1989). Liposomal formulations of pharmaceutical agents are often superior to drugs injected in the free form. When used in the delivery of certain cancer drugs, liposomes help to shield healthy cells from the drugs' toxicity and prevent their concentration in vulnerable tissues (e.g., the kidneys, and liver), lessening or eliminating the common side effects of nausea, fatigue, and hair loss. For instance, liposomal formulations of the anticancer agent vincristine exhibit greater efficacy against L1210 leukemia cells than does free vincristine and have reduced collateral toxicity. Liposomes have also been used to deliver certain vaccines, enzymes, or insulin to the body. They have also been used experimentally to carry normal genes into a cell in order to replace defective, disease-causing genes.

Commercial liposomal drug delivery is gaining attention because of the enhanced stability of liposomes, reduced toxicity, improved pharmacokinetics, enhanced blood circulation time, and increased accumulation of liposomes in the target sites. Reduction in toxicity may result from the ability of liposomes to decrease drug exposure, and subsequent damage, to susceptible tissues (Allen et al. 1991). In fact, the first liposomal drug oncology formalations approved for medicinal use, were of the anthracyclines daunorubicin (DaunoXome; Nextstar Pharmaceuticals, Boulder, Colo.), EVACET (The Liposome Company, Inc., Princeton, N.J.) and DOX [Doxil; Alza Corporation, Palo Alto, Calif. (CAELYX in Europe)].

The use of liposomes as a vehicle of drug delivery has produced many promising results. Major advances in improving the therapeutic index of amphotericin B encapsulated in liposomes have been demonstrated in counteracting systemic fungal infections in cancer patients (Olsen et al. 1982). The liposomal entrapment of this antifungal drug causes a remarkable reduction in toxicity. Liposomes have also been found to be effective in delivering doxorubicin (Williams et al. 1993), vincristine (Woodle et al. 1992), vinblastine, actinomycin-D, arabinoside, cytosine, daunomycin (Julliano and Stamp 1978), mitoxantrone, epirubicin, daunorubicin, (Madden et al 1990) and paclitaxel (Suffness 1995). In a liposomal drug delivery system, if the drug is highly hydrophobic, it tends to associate mainly with the bilayer compartment (Sharma et al., 1995, 1997).

Several methods have been utilized for the production of liposomes. Because vesiculation of natural phospholipid bilayers is not a spontaneous process, physical and chemical methods are used to produce well-defined liposomes from hydrated lipids. Usually, these methods require the input of high energy (e.g., ultrasonic treatment, high pressure, and/or elevated temperatures) to disperse low critical micelle concentration phospholipids as a metastable liposome phase (Lasic and Paphadjopoulos 1998).

One method for the preparation of liposomes involves the solvent evaporation of an oil-in-water emulsion. The oil-phase contains one or more pharmaceutical agents, cholesterol and lipids and the aqueous phase contains an emulsifier. An emulsion consists of two immiscible liquids (usually oil and water), with one of the liquids dispersed as small spherical droplets in the other.

In addition to having utility for drug delivery, liposome-like emulsions can be found in several foods, such as mayonnaise, milk, margarine, and butter. In most foods that contain emulsions of oil and water, the diameters of the droplets usually lie somewhere between 0.1 and 100 μm (Dickinson and Stainsby, 1982, Dickinson, 1992). An emulsion can be conveniently classified according to the distribution of the oil and aqueous phases. A system that consists of oil droplets dispersed in an aqueous phase is called an oil-in-water or O/W emulsion (e.g., mayonnaise, milk, cream etc.). A system that consists of water droplets dispersed in an oil phase is called a water-in-oil or W/O emulsion (e.g., margarine, butter and spreads). The process of converting two separate immiscible liquids into an emulsion, or of reducing the size of the droplets in a preexisting emulsion, is known as homogenization.

In both liposomes used for drug delivery and emulsions in food products, the breakdown of the vesicle structure of the compositions has been observed. The term "emulsion stability" is broadly used to describe the ability of an emulsion to resist changes in its properties with time. Emulsions may become unstable through a variety of physical processes including creaming, sedimentation, flocculation, coalescence, and phase inversion. Creaming and sedimentation are both forms of gravitational separation. Creaming describes the upward movement of droplets due to the fact that they have a lower density than the surrounding liquid, whereas sedimentation describes the downward movement of droplets due to the fact that they have a higher density than the surrounding liquid. Flocculation and coalescence are both types of droplet aggregation. Flocculation occurs when two or more droplets come together to form an aggregate in which the droplets retain their individual integrity, whereas coalescence is the process where two or more droplets merge together to form a single larger droplet. Extensive droplet coalescence can eventually lead to the formation of a separate layer of oil on top of a sample, which is known as "oiling off".

Thermodynamics are largely responsible for the separation of phases. If an emulsion is generated by homogenizing pure oil and pure water together, the two phases will rapidly separate into a system that consists of a layer of oil (lower density) on top of a layer of water (higher density). This is because droplets tend to merge with their neighbors, which eventually leads to complete phase separation.

The disruption of liposome structure over time and premature drug leakage present significant, and potentially very hazardous, problems for using liposomes as vehicles for drug delivery. Drug leakage from liposomes during long-term storage, lyophilization and reconstitution can decrease the predictability and increase the toxicity of drug delivery using liposomes. Specifically, the premature release and leakage of the drug from the liposome results in a faster distribution of the drug in the plasma component, increased toxicity, and decreased concentrations of the drug released at the tumor site. Furthermore, for pegylated liposomal doxorubicin, a novel dose-limiting form of skin toxicity known as palmar-plantar erythrodysaesthesia or hand-foot syndrome has been described (Gordon et al. 1995). Thus a need exists to improve liposome design to increase liposome stability and eliminate premature drug leakage.

In the food industry, the use of emulsifiers and/or thickening agents have been used to produce more stable emulsions. Emulsions usually are thermodynamically unstable systems. It is possible to form emulsions that are kinetically stable (metastable) for a reasonable period of time (a few minutes, hours, days, weeks, months, or years) by including substances known as emulsifiers and/or thickening agent prior to homogenization.

Emulsifiers are surface-active molecules that adsorb to the surface of freshly formed droplets during homogenization, forming a protective membrane that prevents the droplets from coming close enough together to aggregate. Most emulsifiers are molecules having polar and nonpolar regions in the same molecule. The most common emulsifiers used in the food industry are amphiphilic proteins, small-molecule surfactants, and monoglycerides, such as sucrose esters of fatty acids, citric acid esters of monodiglycerides, salts of fatty acids, etc (Krog, 1990).

Thickening agents are ingredients that are used to increase the viscosity of the continuous phase of emulsions and they enhance emulsion stability by retarding the movement of the droplets. A stabilizer is any ingredient that can be used to enhance the stability of an emulsion and may therefore be either an emulsifier or thickening agent.

An efficient emulsifier produces an emulsion in which there is no visible separation of the oil and water phases over time. Phase separation may not become visible to the human eye for a long time, even though some emulsion breakdown has occurred. A more quantitative method of determining emulsifier efficiency is to measure the change in the particle size distribution of an emulsion with time. An efficient emulsifier produces emulsions in which the particle size distribution does not change over time, whereas a poor emulsifier produces emulsions in which the particle size increases due to coalescence and/or flocculation. The kinetics of emulsion stability can be established by measuring the rate at which the particle size increases with time.

In oil-in-water emulsions, proteins are used mostly as surface active agents and emulsifiers. One of the food proteins used in o/w emulsions is whey proteins. The whey proteins include four proteins: β-lactoglobulin, α-lactalbumin, bovine serum albumin and immunoglobulin (Tomberg, 1990). Commercially, whey protein isolates (WPI) with isoelectric point ~5 (Tomberg, 1990) are used for o/w emulsion preparation. According to Hunt (1995), whey protein concentrations of 8% have been used to produce self-supporting gels. Later on, the limiting concentrations of whey protein to produce self-supporting gels are known to be reduced to 4–5%. It is possible to produce gels at whey protein concentrations as low as 2% w/w, using heat treatments at 90° C. or 121° C. and ionic strength in excess of 50 mM (Hunt et al, 1995).

Proteins derived from whey are widely used as emulsifiers in the food industry (Phillips et al, 1994; Dalgleish, 1996). They adsorb to the surface of oil droplets during homogenization and form a protective membrane, which prevents droplets from coalescing. The physicochemical properties of emulsions stabilized by whey protein isolates (WPI) are related to the aqueous phase composition (e.g, ionic strength and pH) and the processing and storage conditions of the product (e.g, heating, cooling, and mechanical agitation). Emulsions are prone to flocculation around the isoelectric point of the WPI, but are stable at higher or lower pH (Philips et al, 1994). The resistance to flocculation may be interpreted in terms of colloidal interactions between droplets, i.e, van der Waals, electrostatic repulsion and steric forces (Philips et al, 1994; Dalgleish, 1996). The van der Waals interactions are fairly long-range. Electrostatic interactions between similarly charged droplets are repulsive, and their magnitude and range decrease with increasing ionic strength. Short range interactions become important at droplet separations of the order of the thickness of the interfacial layer or less (e.g., steric, thermal fluctuation and hydration forces; Israelachvili, 1992). Such interactions are negligible at distances greater than the thickness of the interfacial layer, but become strongly repulsive when the layers overlap, preventing droplets from getting closer.

Although emulsifiers and thickening agents have been successfully used in the food industry, there is still a significant need for improving drug-delivering liposome stability. Because most small-molecule chemotherapeutic agents have widespread distribution via i.v. administration (Chanber and Longo, 1996; Speth et al., 1988), this results in a narrow therapeutic index due to a high level of toxicity in healthy tissues. A method for producing more stable liposomes would result in more consistent pharmacokinetics while retaining the advantages of liposomal delivery.

SUMMARY OF THE INVENTION

The present invention overcomes deficiencies in the prior art by protecting lipid formulations, preferably liposomes, with protein molecules to minimize or eliminate drug leakage from the liposome. Specifically, the present invention provides a method of preparing a protein-stabilized lipid formulation containing at least one lipophilic pharmaceutical agent, the method comprising: preparing an organic solution comprising one or more phospholipids, mixing at least one pharmaceutical agent into said organic solution, infusing said organic mixture into an aqueous solution comprising an emulsion-forming protein to form an emulsion, and removing organic solvent from said emulsion to form the protein-stabilized lipid formulation.

In one embodiment of the invention, the lipid formulation in this method comprises protein-stabilized liposomes. In another embodiment of the invention, the liposome-forming components further includes cholesterol. The liposome-forming components may include a PEG-phospholipid. In certain embodiments of the invention, the PEG-phospholipid comprises poly(ethylene glycol)-derivatized distearoylphosphatidylethanolamine (PEG-DSPE) and/or poly (ethylene glycol)-derivatized ceramides (PEG-CER). The lipophilic pharmaceutical agent is further identified as a substantially water insoluble pharmaceutical agent. Using the method of the present invention, the phospholipid and lipophilic pharmaceutical agent may be included in the organic solution at a ratio ranging from about 0.01:25 to about 1:10 drug:lipid (w/w).

The present invention preferably uses an emulsion forming protein. In certain embodiments of the present invention, said emulsion forming protein comprises an albumin, immunoglobulin, casein, insulin, hemoglobin, lysozyme, immunoglobulin, α-2-macroglobulin, fibronectin, vitronectin, fibrinogen, lipase, or enzyme. In one embodiment of the invention, the preferred emulsion forming protein is an albumin.

The pH of the aqueous solution may also vary in the present invention. In one embodiment of the present invention, the said aqueous solution is at a pH of between about 6.0 and 7.6. In some embodiments of the present invention, the emulsion-forming protein comprises from about 0.1% to about 20% (w/v), more preferably from about 1% to about 10% (w/v), of the aqueous solution.

The emulsion is preferably formed by steps that comprise: agitating said mixture at between about 1000 and about 24,000 revolutions per minute, more preferably 3000 and about 10,000 revolutions per minute, and subjecting the agitated mixture to high pressure microfluidization or homogenization at 5,000 to 30,000 PSI, more preferably 10,000 to 30,000 PSI. In certain embodiments of the invention, the mixture may be agitated using a homogenizer, such as a rotary homogenizer. In other embodiments of the invention, the lipid formulation is filtered; for example, the lipid formulation may be filtered through a 0.20 or 0.22 micron filter. In other embodiments, the lipid formulation is lyophilized to provide a powder suitable for reconstitution in an aqueous suspension; for example, the lipid formulation may be lyophilized in the presence of one or more cryoprotectants, such as sucrose, mannitol or trehalose.

The pharmaceutical agent preferably comprises a cardiovascular drug, respiratory drug, sympathomimetic drug, cholinomimetic drug, adrenergic or adrenergic neuron blocking drug, analgesic/antipyretic, anesthetic, antiasthamatic, antibiotic, antidepressant, antidiabetic, antifungal agent, antihypertensive agent, anti-inflammatory, antineoplastic, antianxiety agent, immunosuppressive agent, antimigraine agent, sedatives/hypnotic, antianginal agent, antipsychotic agent, antimanic agent, antiarrhythmic, antiarthritic agent, antigout agent, anticoagulant, thrombolytic agent, antifibrinolytic agent, hemorheologic agent, antiplatelet agent, anticonvulsant, antiparkinson agent, antihistamine/antipruritic, agent useful for calcium regulation, antibacterial agent, antiviral agent, antimicrobial, anti-infective, bronchodialator, hormone, hypoglycemic agent, hypolipidemic agent, protein, nucleic acid, agent useful for erythropoiesis stimulation, antiulcer/antireflux agent, antinauseant/antiemetic, oil-soluble vitamin, mitotane, visadine, halonitrosourea, anthrocycline or ellipticine. In various embodiments of the invention, the pharmaceutical agent is Proscillaridin-A, oleandrin, digitoxin, digoxin, odoroside-A, colchicine, colchicine derivatives, ara-C derivatives, diphyllin, justicidin-A, diphyllin derivatives, cleistanthin A, chloroquine, amphotericin B, paclitaxel, docetaxel, cyclosporine, camptothecin, 7-ethyl-10-hydroxy-camptothecin, 10-hydroxy-camptothecin, a camptothecin derivative, podophyllotoxin, podophyllotoxin derivatives, vinblastine, vincristine, dihydroartemisinin, mitoxantrone, amphotericin B, epothilone-A, epothilone-B, epothilone-C, epothilone-D, an epothilone derivative, a benz[c]-phenanthridine alkaloid derivative, a chelerythrine alkaloid derivative or cisplatin.

Phopholipids are preferably used to create the lipid formulations, preferably liposomes, of the present invention. One or more of said phospholipids preferably comprise one or more of hydrogenated soy phosphatidylcholine (HSPC), egg phosphatidylcholine (EPC), phosphatidylethanolamine (PE), phosphatidylglycerol (PG), phosphatidylinsitol (PI), monosialogangolioside, spingomyelin (SPM), distearoylphosphatidylcholine (DSPC), dimyristoylphosphatidylcholine (DMPC), or dimyristoylphosphatidylglycerol (DMPG). In certain embodiments of the invention, the ratio of pharmaceutical agent to lipid-protein ranges from about 0.0005 to about 1 (w/w), more preferably about 0.0005 to about 0.5 (w/w), more preferably about 0.001 to about 0.1 (w/w).

Methods for physically mixing the lipid formulation to produce nanoparticles may also be used with the present invention. In certain embodiments of the invention, the lipid formulation is subjected to high shear stress to reduce particle size. Specifically, the lipid formulation is preferably defined further as comprising nanoparticles having size less than about 220 nm, more preferably between about 80–160 nm, more preferably between about 100–120 nm.

The present invention also includes a protein-stabilized lipid formulation comprising a lipophilic pharmaceutical agent, the formulation prepared by any of the processes stated above.

Another embodiment of the invention includes a method of treating a disease in a patient comprising: obtaining a lipophilic pharmaceutical agent drug indicated for treatment of the disease, preparing a protein-stabilized lipid formulation of said pharmaceutical agent; and administering an amount of the lipid formulated pharmaceutical agent to said patient that is effective to treat the disease. In this aspect of the invention, the protein-stabilized lipid formulation of said pharmaceutical agent is prepared in accordance with the methods stated above. In certain embodiments, the disease is a hyperproliferative disease and the pharmaceutical agent is an anti-hyperproliferative agent. In certain embodiments of the invention, the formulation is administered parenterally; preferably by slow infusion or bolus injection.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present invention overcomes deficiencies in the prior art relating to liposomes by protecting liposomes with protein molecules to minimize or eliminate drug leakage from the liposome. As the protein uniformly coats or forms a shell around the liposome, the drug is protected from any further degradation of the liposome. The method of the present invention can also be used for the entrapment of a high concentration of drug inside the liposome compartment.

I. Definitions

Lipid formulations include emulsions and liposomes. Liposomes include: multivesicular liposomes, multilamellar liposomes, and unilamellar liposomes.

As used herein, the term "micron" refers to a unit of measure of one one-thousandth of a millimeter.

As used herein, the term "biocompatible" describes a substance that does not appreciably alter or affect in any adverse way, the biological system into which it is introduced.

As used herein, the terms "cell proliferative diseases" or "hyperproliferative diseases" refer to disorders resulting from abnormally increased and/or uncontrolled growth of cell(s) in a multicellular organism that results in harm (e.g., discomfort or decreased life expectancy) to the multicellular organism. Cell proliferative diseases can occur in animals or humans. Cancer is an example of a cell proliferative disease, and certain embodiments of the present invention relate to the treatment of cancer.

"Emulsion forming protein" refer to any protein that adsorb to the surface of freshly formed lipid formulation droplets (preferably liposomal droplets) during homogenization, forms a protective membrane that prevents the lipid formulation droplets (preferably liposomal droplets) from coming close enough together to aggregate, increases the viscosity of the continuous phase of lipid formulations (preferably emulsions, more preferably liposomes), or enhances the stability of lipid formulations (preferably emulsions, more preferably liposomes) by retarding the movement of the lipid formulation droplets.

II. Lipid Formulations

The present invention relates to lipid formulations. Lipid formulations include emulsions and liposomes.

a. Liposomes

The present invention provides a method for protein stabilized liposome (PSL) nanoparticle formulations of substantially water insoluble pharmaceutical agents and methods of preparing and employing such formulations. The advantages of these PSL nanoparticle formulations are that a substantially water insoluble pharmaceutical agent is entrapped in either dissolved or precipitated form. These compositions have been observed to provide a very low toxicity form of the pharmacologically active agent that can be delivered in the form of nanoparticles or suspensions by slow infusions or by bolus injection or by other parenteral or oral delivery routes. These PSL nanoparticles have sizes below 400 nm, preferably below 200 nm, and more preferably below 120 nm having hydrophilic proteins coated onto the surface of the nanoparticles.

Phospholipids preferably form an important part of liposomes. Phospholipids are, in their simplest form, composed of glycerol bonded to two fatty acids and a phosphate group. The resulting compound called phosphatidic acid contains a region (the fatty acid component) that is fat-soluble along with a region (the charged phosphate group) that is water-soluble. Most phospholipids also have an additional chemical group bound to the phosphate. For example, it may be connected with choline; the resulting phospholipid is called phosphatidylcholine, or lecithin. Other phospholipids include phosphatidylglycerol, phosphatidylinositol, phosphatidylserine, and phosphatidylethanolamine. The fat-soluble portions associate with the fat-soluble portions of other phospholipids while the water-soluble regions remain exposed to the surrounding solvent. The phospholipids of the cell membrane form into a sheet two molecules thick with the fat-soluble portions inside shielded on both sides by the water-soluble portions. This stable structure provides the cell membrane with its integrity.

The components of liposomes determine the physical characteristics of the liposome. Liposomes preferably consist of amphipathic lipid molecules, with phospholipids being the major component. Most commonly, phosphatidylcholine is used as the primary constituent. Other lipids, including phosphatidylethanolamine, phosphatidylserine, sphingomyelin, glycolipids and sterols are often added. The physical characteristics of liposomes depend on pH, ionic strength and phase transition temperatures. The phase transition consists of a closely packed, ordered structure, called as the gel-state, to a loosely packed, less-ordered structure, known as the fluid state. The phase transition temperature ($T_c$) depends on the acyl chain length, degree of saturation, and polar head group. For example, the $T_c$ of egg phosphatidylcholine with a high degree of unsaturation of the acyl chains and varying chain length is $-15°$ C. However, in a fully saturated distearoylphosphatidylcholine (DSPC), $T_c$ is over $50°$ C. Most liposomal formulations contain cholesterol in order to form a more closely packed bilayer system during preparation. Cholesterol addition to phosphatidylcholine changes the melting behavior of the bilayer, as cholesterol tends to eliminate the phase transition. Cholesterol addition has a condensing effect on the fluid-state bilayer and strongly reduces bilayer permeability.

b. Emulsions

The present invention can also be employed using emulsions. Most emulsions can be considered to comprise three regions that have different physicochemical properties: the interior of the droplets, the continuous phase, and the interface. The molecules in an emulsion distribute themselves among these three regions according to their concentration and polarity (Wedzicha, 1988). Nonpolar molecules tend to be located primarily in the oil phase, polar molecules in the aqueous phase, and amphiphilic molecules at the interface. It should be noted that even at equilibrium, there is a continuous exchange of molecules between the different regions, which occurs at a rate that depends on the mass transport of the molecules through the system. Molecules may also move from one region to another when there is some alteration in the environmental conditions of an emulsion (e.g, a change in temperature or dilution within the mouth). The location and mass transport of the molecules within an emulsion have a significant influence on the aroma, flavor release, texture, and physicochemical stability of food products (Dickinson and Stainsby, 1982, Wedzicha et al, 1991, Coupland and McClements, 1996).

Many properties of emulsions can only be understood with reference to their dynamic nature. The formation of emulsions by homogenization is a highly dynamic process which involves the violent disruption of droplets and the rapid movement of surface-active molecules from the bulk liquids to the interfacial region. Even after their formation, the droplets in an emulsion are in continual motion and frequently collide with one another because of their Brownian motion, gravity, or applied mechanical forces (Melik and Fogler, 1988, Dukhin and Sjoblorn, 1996). The continual movement and interactions of droplets cause the properties of emulsions to evolve over time due to the various destabilization processes such as change in temperature or in time.

Often, the most important properties of emulsion are determined by the size of the droplets they contain (Dickinson and Stainsby, 1982, Dickinson, 1992). Consequently, it is important to control, predict and measure, the size of the droplets in emulsions. If all the droplets in an emulsion are of the same size, the emulsion is referred to as monodisperse, but if there is a range of sizes present, the emulsion is referred to as polydisperse. The size of the droplets in a monodisperse emulsion can be completely characterized by a single number, such as the droplet diameter (d) or radius (r). Monodisperse emulsions are sometimes used for fundamental studies because the interpretation of experimental measurements is much simpler than that of polydisperse emulsions. Nevertheless, emulsions by homogenization always contain a distribution of droplet sizes, and so the specification of their droplet size is more complicated than that of monodisperse systems. Ideally, one would like to have information about the full particle size distribution of an emulsion (i.e, the size of each of the droplets in the system). In many situations, knowledge of the average size of the droplets and the width of the distribution is sufficient (Hunter, 1986).

III. Protein Stabilized Liposomes (PSL)

The present invention is directed in one important aspect, to the use of PSL nanoparticle formulations containing pharmaceutical agents in the treatment of various diseases in humans, including the cell-proliferation disease, cancer. More particularly, the invention is directed to the use of novel PSL nanoparticle formulations with reduced toxicity, long-circulating time in the bloodstream and able to deliver the drug to the target sites such as tumor sites. These PSL nanoparticle formulations are higher than or substantially equivalent in efficacy to each one of the pharmaceutical agents in its free form, yet generally have low toxicity. In another aspect, the present invention provides compositions and methods which are useful for the treatment of solid tumors in a host and which are also useful for increasing the therapeutic index of each one of the anticancer agents in a host. The pharmaceutical compositions are PSL nanoparticle formulations comprising a mixture of egg phosphatidylcholine (EPC), hydrogenated soy phosphatidylcholine (HSPC), phosphatidylethanolamine (PE), phosphatidylglycerol (PG), phosphatidylinsitol (PI), monosialoganglioside and sphingomyelin (SPM); the derivatized vesicle forming lipids such as poly(ethylene glycol)-derivatized distearoylphosphatidylethanolamine (PEG-DSPE), poly(ethylene glycol)-derivatized ceramides (PEG-CER), distearoylphosphatidylcholine (DSPC), dimyristoyl-phosphatidylcholine (DMPC), dimyristoylphosphatidylglycerol (DMPG), and dipalmitoylphosphatidylcholine (DPPC), cholesterol, and proteins.

Many kinds of lipids may be used to create liposomes. The vesicle forming lipids include: egg phosphatidylcholine (EPC), hydrogenated soy phosphatidylcholine (HSPC), phosphatidylethanolamine (PE), phosphatidylglycerol (PG), phosphatidylinsitol (PI), monosialogangolioside and spingomyelin (SPM); the derivatized vesicle forming lipids such as poly(ethylene glycol)-derivatized distearoylphosphatidylethanolamine (PEG-DSPE) and/or poly(ethylene glycol)-derivatized ceramides (PEG-CER); and cholesterol are dissolved in organic solvents along with one or more substantially water insoluble pharmaceutical agent. The phospholipids can be either synthetic or derived from natural sources such as egg or soy. The phospholipids can be distearoylphosphatidylcholine (DSPC), dimyristoyl-phosphatidylcholine (DMPC), dimyristoylphosphatidylglycerol (DMPG), and dipalmitoylphosphatidylcholine (DPPC). In order to make the protein stabilized liposomal nanoparticles, substantially water insoluble pharmaceutical agent, lipid and other agents are dissolved in a suitable solvent (e.g., chloroform, methylene chloride, ethyl acetate, ethanol, tetrahydrofuran, dioxane, acetonitrile, acetone, dimethyl sulfoxide, dimethyl formamide, methylpyrrolidinone, or the like, as well as mixtures of any two or more thereof). The substantially water insoluble pharmaceutical agent to lipid-protein weight ratio varies between 0.01 and 1, preferably between 0.1 and 1. Additional solvents contemplated for use in the practice of the present invention include soybean oil, coconut oil, olive oil, safflower oil, cotton seed oil, sesame oil, orange oil, limonene oil, C1–C20 alcohols, C2–C20 esters, C3–C20 ketones, polyethylene glycols, aliphatic hydrocarbons, aromatic hydrocarbons, halogenated hydrocarbons and combinations thereof.

An emulsion forming protein is preferably used to generate the PSL. In one embodiment, to generate protein stabilized liposomal nanoparticles, a protein (e.g., human serum albumin) is added (into the aqueous phase) to act as a stabilizing agent or an emulsifier for the formation of stable nanodroplets. The emulsion forming protein is preferably added at a concentration in the range of about 0.05 to 25% (w/v), more preferably in the range of about 0.5%–5% (w/v).

For the production of the protein stabilized liposomal nanoparticles, an emulsion is preferably formed by homogenization under high pressure and high shear forces. Such homogenization is preferably carried out in a high pressure homogenizer, typically operated at pressures in the range of about 3,000 up to 30,000 psi. Preferably, such processes are carried out at pressures in the range of about 6,000 up to 25,000 psi. The resulting emulsion comprises very small nanodroplets of the nonaqueous solvent containing the substantially water insoluble pharmaceutical agent, lipid and other agents. Acceptable methods of homogenization include processes imparting high shear and cavitation such as high pressure homogenization, high shear mixers, sonication, high shear impellers, and the like.

Finally, the solvent is preferably evaporated under reduced pressure to yield a colloidal system composed of protein stabilized liposomal nanoparticles of substantially water insoluble pharmaceutical agent in liposome and protein. Acceptable methods of evaporation include the use of rotary evaporators, falling film evaporators, spray driers, freeze driers, and the like. Following evaporation of solvent, the liquid suspension may be dried to obtain a powder containing the pharmacologically active agent and protein. The resulting powder can be redispersed at any convenient time into a suitable aqueous medium such as saline, buffered saline, water, buffered aqueous media, solutions of amino acids, solutions of vitamins, solutions of carbohydrates, or the like, as well as combinations of any two or more thereof, to obtain a suspension that can be administered to mammals. Methods contemplated for obtaining this powder include freeze-drying, spray drying, and the like.

In accordance with a specific embodiment of the present invention, there is provided a method for the formation of unusually small submicron liposomal particles containing a substantially water insoluble pharmaceutical agent, i.e., particles which are less than 200 nanometers in diameter. Such particles are capable of being sterile-filtered before use in the form of a liquid suspension. The ability to sterile-filter the end product of the invention formulation process (i.e., the substantially water insoluble pharmaceutical agent particles) is of great importance since it is impossible to sterilize dispersions which contain high concentrations of protein (e.g., serum albumin) by conventional means such as autoclaving.

Sterile-filterable protein stabilized liposomal particles of substantially water insoluble pharmaceutical agents (i.e., particles<200 nm) are preferably formed by dissolving the substantially water insoluble pharmaceutical agent, lipids, and other agents in a substantially water immiscible organic solvent (e.g., a solvent having less than about 5% solubility in water, such as, for example, chloroform) at a high concentration, thereby forming an oil phase containing the substantially water insoluble pharmaceutical agent, lipids and other agents. Preferred solvents are set forth herein. Next, a water miscible organic solvent (e.g., a solvent having greater than about 10% solubility in water, such as, for example, ethanol) is added to the oil phase at a final concentration in the range of about 1%–99% v/v, more preferably in the range of about 5%–25% v/v of the total organic phase. The water miscible organic solvent can be selected from such solvents as ethyl acetate, ethanol, tetrahydrofuran, dioxane, acetonitrile, acetone, dimethyl sulfoxide, dimethyl formamide, methylpyrrolidinone, and the like. Alternatively, the mixture of water immiscible solvent with the water miscible solvent is prepared first, followed by dissolution of the substantially water insoluble pharmaceutical agent, lipids and other agents in the mixture.

In the next stage, human serum albumin or any other suitable stabilizing agent as described above is preferably dissolved in aqueous media. This component acts as a stabilizing agent for the formation of stable nanodroplets. Optionally, a sufficient amount of the first organic solvent (e.g. chloroform) is dissolved in the aqueous phase to bring it close to the saturation concentration. A separate, measured amount of the organic phase (which now contains the substantially water insoluble pharmaceutical agents, the first organic solvent and the second organic solvent) is added to the saturated aqueous phase, so that the phase fraction of the organic phase is between about 0.5%–015% v/v, and more preferably between 1% and 8% v/v. Next, a mixture composed of micro and nanodroplets is preferably formed by homogenization at low shear forces. This can be accomplished in a variety of ways, as can readily be identified by those of skill in the art, employing, for example, a conventional laboratory homogenizer operated in the range of about 2,000 up to about 15,000 rpm. This is preferably followed by homogenization under high pressure (i.e., in the range of about 3,000 up to 30,000 psi). The resulting mixture comprises an aqueous protein solution (e.g., human serum albumin), the substantially water insoluble pharmaceutical agent, lipids, other agents, the first solvent and the second solvent. Finally, the solvent is preferably rapidly evaporated under vacuum to yield a colloidal dispersion system (liposomal substantially water insoluble pharmaceutical agent and protein) in the form of extremely small nanoparticles (i.e., particles in the range of about 50 nm–200 nm diameter), and thus can be sterile-filtered. The preferred size range of the particles is between about 50 nm–170 nm, depending on the formulation and operational parameters.

The protein stabilized liposomal nanoparticles prepared in accordance with the present invention may be further converted into powder form by removal of the water therefrom, e.g., by lyophilization at a suitable temperature-time profile. The protein (e.g., human serum albumin) itself acts as a cryoprotectant, and the powder can easily be reconstituted by addition of water, saline or buffer, without the need to use such conventional cryoprotectants as mannitol, sucrose, glycine, and the like. While not required, it is of course understood that conventional cryoprotectants may be added to invention formulations if so desired. The liposomal shell containing the substantially water insoluble pharmaceutical agent allows for the delivery of high doses of the pharmacologically active agent in relatively small volumes.

According to this embodiment of the present invention, the liposome containing substantially water insoluble pharmaceutical agent preferably has a cross-sectional diameter of no greater than about 10 microns. A cross-sectional diameter of less than 5 microns is more preferred, while a cross-sectional diameter of less than 1 micron is presently the most preferred for the intravenous route of administration.

Proteins contemplated for use as stabilizing agents and/or emulsion forming proteins in accordance with the present invention include albumins (which contain 35 cysteine residues), immunoglobulins, caseins, insulins (which contain 6 cysteines), hemoglobins (which contain 6 cysteine residues per $\alpha 2$ $\beta 2$ unit), lysozymes (which contain 8 cysteine residues), immunoglobulins, $\alpha$-2-macroglobulin, fibronectins, vitronectins, fibrinogens, lipases, and the like. Proteins, peptides, enzymes, antibodies and combinations thereof, are general classes of stabilizers contemplated for use in the present invention. A presently preferred protein for use is albumin. Specific antibodies may also be utilized to target the nanoparticles to specific locations.

In the preparation of invention compositions, a wide variety of organic media can be employed to suspend or dissolve the substantially water insoluble substantially water insoluble pharmaceutical agents. Organic media contemplated for use in the practice of the present invention include any nonaqueous liquid that is capable of suspending or dissolving the pharmacologically active agent, but does not chemically react with either the polymer employed to produce the shell, or the pharmacologically active agent itself. Examples include vegetable oils (e.g., soybean oil, olive oil, and the like), coconut oil, safflower oil, cotton seed oil, sesame oil, orange oil, limonene oil, aliphatic, cycloaliphatic, or aromatic hydrocarbons having 4–30 carbon atoms (e.g., n-dodecane, n-decane, n-hexane, cyclohexane, toluene, benzene, and the like), aliphatic or aromatic alcohols having 2–30 carbon atoms (e.g., octanol, and the like), aliphatic or aromatic esters having 2–30 carbon atoms (e.g., ethyl caprylate (octanoate), and the like), alkyl, aryl, or cyclic ethers having 2–30 carbon atoms (e.g., diethyl ether, tetrahydrofuran, and the like), alkyl or aryl halides having 1–30 carbon atoms (and optionally more than one halogen substituent, e.g., $CH_3Cl$, $CH_2Cl_2$, $CH_2Cl$—$CH_2Cl$, and the like), ketones having 3–30 carbon atoms (e.g., acetone, methyl ethyl ketone, and the like), polyalkylene glycols (e.g., polyethylene glycol, and the like), or combinations of any two or more thereof.

Especially preferred combinations of organic media contemplated for use in the practice of the present invention typically have a boiling point of no greater than about 200° C., and include volatile liquids such as dichloromethane, chloroform, ethyl acetate, benzene, and the like (i.e., solvents that have a high degree of solubility for the pharmacologically active agent, and are soluble in the other organic medium employed), along with a higher molecular weight (less volatile) organic medium. When added to the other organic medium, these volatile additives help to drive the solubility of the pharmacologically active agent into the organic medium. This is desirable since this step is usually time consuming. Following dissolution, the volatile component may be removed by evaporation (optionally under vacuum).

The liposomes containing substantially water insoluble pharmaceutical agent stabilized with protein, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

For increasing the long-term storage stability, the PSL nanoparticle formulations may be frozen and lyophilized in the presence of one or more protective agents such as sucrose, mannitol, trehalose or the like. Upon rehydration of the lyophilized PSL nanoparticle formulations, the suspension retains essentially all the substantially water insoluble pharmaceutical agent previously loaded and the particle size. The rehydration is accomplished by simply adding purified or sterile water or 0.9% sodium chloride injection or 5% dextrose solution followed by gentle swirling of the suspension. The potency of the substantially water insoluble pharmaceutical agent in a PSL nanoparticle formulation is not lost after lyophilization and reconstitution.

The PSL nanoparticle formulation of the present invention is shown to be less toxic than the substantially water insoluble pharmaceutical agent administered in its free form. In the present invention, efficacy of PSL nanoparticle formulations of the present invention with varying lipid compositions, particle size, and substantially water insoluble pharmaceutical agent to lipid-protein ratio have been investigated on various systems such as human cell lines and animal models for cell proliferative activities. Furthermore, effects of PSL nanoparticle formulations and various substantially water insoluble pharmaceutical agents in their free form on the body weight of mice with different sarcomas and healthy mice without tumor have been investigated. Effects of PSL nanoparticle formulations and various substantially water insoluble pharmaceutical agents in their free form on the DNA fragmentation in different normal and tumor cells are investigated. These examples are not intended, however, to limit or restrict the scope of the present invention in any way and should not be construed as providing conditions, parameters, reagents, or starting materials which must be utilized exclusively in order to practice the art of the present invention.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Preparation of PSL-Proscillaridin-A

A lipid mixture containing DSPC: cholesterol: PEG2000-DSPE (Northern Lipids Ltd, Canada) in a molar ratio of about 55:40:5 was dissolved in a chloroform: ethanol mixture. For example, 600 mg of DSPC, 208 mg cholesterol and 100 mg PEG2000-DSPE were dissolved in 6 mL of chloroform: and 0.7 mL of ethanol (9.0:1.0 vol/vol) mixture. 70 mg of Proscillaridin-A (Sigma-Aldrich Co, USA) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

The above method has also been used for preparing PSL-nanoparticle formulations containing other cardiac glycosides oleandrin, odoroside-A, neriifolin and digitoxin.

EXAMPLE 2

Preparation of PSL-N-Pentanoyl-deacetyl-colchicine

Figure 1:
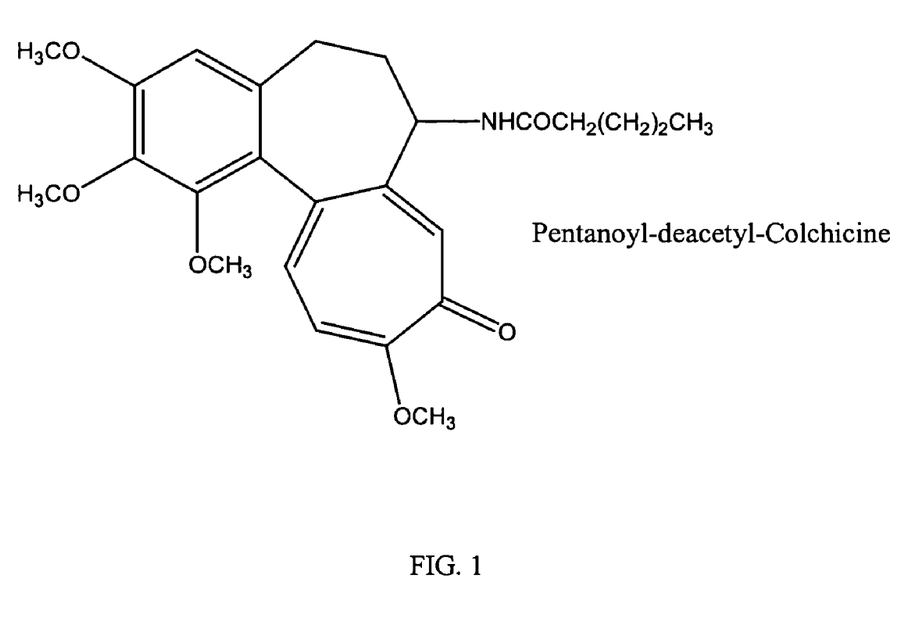
FIG. 1: The chemical structure of N-Pentanoyl-deacetyl colchicine.

A lipid mixture containing DSPC: cholesterol: PEG2000-DSPE (Northern Lipids Ltd, Canada) in a molar ratio of about 55:40:5 was dissolved in a chloroform: ethanol (about 8.5:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 70 mg of N-Pentanoyl-deacetyl-colchicine (Synthesized from colchicine using known procedure, structure in FIG. 1) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with an IKA homogenizer at 6000–10000 RPM (IKA Works, Germany).

The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

In a similar manner, the above method has also been used for preparing PSL-nanoparticle formulations containing other colchicine derivatives N-(1-Adamantanecarboxyl)-deacetyl-colchicine and N-(cyclohexylacetyl)-deacetyl-colchicine.

EXAMPLE 3

Preparation of PSL-Paclitaxel

A lipid mixture containing DSPC: cholesterol: PEG2000-DSPE (Northern Lipids Ltd, Canada) in a molar ratio of about 55:40:5 was dissolved in a chloroform: ethanol (about 8.5.:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 100 mg of Paclitaxel (obtained from China) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 4

Preparation of PSL-Cyclosporine

A lipid mixture containing DSPC: cholesterol: PEG2000-DSPE (Northern Lipids Ltd, Canada) in a molar ratio of about 55:40:5 was dissolved in a chloroform: ethanol (about 8.5.:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 100 mg of Cyclosporine (obtained from China) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 µm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 5

Preparation of PSL-Vinblastine

A lipid mixture containing DSPC: cholesterol: PEG2000-DSPE (Northern Lipids Ltd, Canada) in a molar ratio of about 55:40:5 was dissolved in a chloroform: ethanol (about 8.5.:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 100 mg of Vinblastine (obtained from China) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 6

Preparation of PSL-7-Ethyl-10-Hydroxy-Camptothecin (SN-38)

A lipid mixture containing DSPC: cholesterol: PEG2000-DSPE (Northern Lipids Ltd, Canada) in a molar ratio of about 55:40:5 was dissolved in chloroform. For example, 600 mg of DSPC, 230 mg cholesterol and 100 mg PEG2000-DSPE were dissolved in 6 mL of chloroform. 25 mg of 7-Ethyl-10-Hydroxy-Camptothecin (SN-38) (Abatra Corporation, China) was dissolved in 1.0 mL of Dimethyl Sulfoxide and the solution was added to the above chloroform solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 7

Preparation of PSL-Dihydro-Artemisinin

A lipid mixture containing DSPC: cholesterol: PEG2000-DSPE (Northern Lipids Ltd, Canada) in a molar ratio of about 55:40:5 was dissolved in a chloroform: ethanol (about 8.5.:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 100 mg of Dihydro-Artemisinin (obtained from China) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 8

Preparation of PSL-Podophyllotoxin

A lipid mixture containing DSPC: cholesterol: PEG2000-DSPE (Northern Lipids Ltd, Canada) in a molar ratio of about 55:40:5 was dissolved in a chloroform: ethanol (about 8.5.:1.5 vol/vol) mixture. For example, 600 mg of DSPC, 270 mg cholesterol and 100 mg PEG2000-DSPE were dissolved in 6 mL of chloroform and 0.7 mL of ethanol (9.0:1.0 vol/vol) mixture. 100 mg of Podophyllotoxin (obtained from India) was added to the above chloroform-ethanol solution and shaken until it was dissolved. A 4% human albumin solution was prepared by dissolving 2 gm of human albumin (Sigma-Aldrich Co, USA) in 50 mL of sterile Type I water. The pH of the human albumin solution was adjusted to 6.5–6.7 by adding either 1N hydrochloric acid or 1N sodium hydroxide solution in sterile water. The above organic solution was added to the albumin phase and the mixture was pre-homogenized with a IKA homogenizer at 6000–10000 RPM (IKA Works, Germany). The resulting emulsion was subjected to high-pressure homogenization (Avestin Inc, USA). The pressure was varied between 20,000 and 30,000 psi and the emulsification process was continued for 3–6 passes. During homogenization the emulsion was cooled between 2–5° C. by circulating the coolant through the homogenizer from a temperature controlled heat exchanger (Julabo, USA). This resulted in a homogeneous and extremely fine oil-in-water emulsion. The emulsion was then transferred to a rotary evaporator (Buchi, Switzerland) and rapidly evaporated to a nanoparticle suspension. The evaporator pressure was set during the evaporation by a diaphram vacuum pump (Laboport) at 10–50 mm Hg and the bath temperature during evaporation was set at 50° C.

The particle size of the suspension was determined by photon correlation spectroscopy with a Malvern Zetasizer. The cryoprotectant Trehalose dihydrate (Sigma-Aldrich Co, USA) was added to the suspension so that the concentration of Trahalose dihydrate in the suspension was in the range of 4–9% by weight. The suspension was sterile-filtered through a 0.22 μm filter (Nalgene, USA). The particle size of the suspension was between 30 and 220 nm. The suspension was frozen below −40° C. and lyophilized. The lyophilized cake was reconstituted prior to further use. The particle size did not change appreciably following lyophilization and reconstitution.

EXAMPLE 9

Preparation of PSL-Proscillaridin-A

Lipid mixtures (Egg sphingomyelin:Phosphatidylcholine: cholesterol:PEG2000-DSPE=1:1:1:0.02 molar ratio) were dissolved in a chloroform:ethanol (9.5:0.5 vol/vol) mixture as in Example 1. 100 mg of Proscillaridin-A was added to the above solution, resulting in a drug to lipid ratio of about 1:10 (wt/wt). The above procedure described in Example 1 was employed to prepare PSL-Proscillaridin-A. The particle size of the suspension before lyophilization and after reconstitution was between 50 and 220 nm.

EXAMPLE 10

Preparation of PSL-Proscillaridin-A

The above procedure described in Example 1 was employed to prepare PSL-Proscillaridin-A. However, instead of the lipid, PEG2000-DSPE, PEG2000-ceramide was used. The particle size of the suspension before lyophilization and after reconstitution was between 50 and 220 nm.

EXAMPLE 11

Preparation of PSL-Podophyllotoxin

The above procedure described in Example 8 was employed to prepare PSL-Podophyllotoxin. Lipid mixtures (Distearylphosphatidylcholine:cholesterol:PEG2000-ceramide=1.5:1:0.02 molar ratio) were dissolved in a chloroform:ethanol (8:2 vol/vol) mixture. The particle size of the suspension before lyophilization and after reconstitution was between 50 and 220 mm.

EXAMPLE 12

Preparation of PSL-Digitoxin

The above procedure described in Example 1 was used for the preparation of PSL-Digitoxin. Lipid mixtures (Distearylphosphatidylcholine:cholesterol=2:1 molar ratio) were dissolved in a chloroform:ethanol (8:2 vol/vol) mixture or in chloroform or dicloromethane. The particle size of the suspension before lyophilization and after reconstitution was between 50 and 220 nm.

EXAMPLE 13

Preparation of PSL-Oleandrin

The above procedure described in Example 1 was employed to prepare PSL-Oleandrin. Lipid mixtures (egg phosphatidylcholine: cholesterol=55:45 molar ratio) were dissolved in a chloroform:ethanol (8:2 vol/vol) mixture or in chloroform or dicloromethane. The particle size of the suspension before lyophilization and after reconstitution was between 50 and 220 nm.

EXAMPLE 14

Preparation of PSL-Paclitaxel

The above procedure described in Example 4 was employed to prepare PSL-Paclitaxel. Lipid mixtures (1,2-di (2,4-Tetradecadienoyl)-3-phosphatidylcholine:cholesterol=2:1 molar ratio) were dissolved in a chloroform: ethanol (8:2 vol/vol) mixture or in chloroform or dicloromethane. The particle size of the suspension before lyophilization and after reconstitution was between 50 and 220 nm.

EXAMPLE 15

Preparation of PSL-Proscillaridin-A

The above procedure described in Example 1 was employed to prepare PSL-Proscillaridin-A. However, instead of the lipid, DSPC, egg phospholipid was used. The particle size of the suspension before lyophilization and after reconstitution was between 50 and 220 nm.

EXAMPLE 16

Preparation of PSL-Podophyllotoxin

The above procedure described in Example 9 was employed to PSL-Podophyllotoxin. However instead of the lipid, DSPC, partially hydrogenated phosphatidylcholine was used. The particle size of the suspension before lyophilization and after reconstitution was between 50 and 220 nm.

All of the COMPOSITIONS and METHODS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS and METHODS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Allen T M, Hansen C, Martin F J, Redemann C and Yau-Young A: Liposome containing a synthetic lipid derivative of poly(ethylene glycol) show prolonged circulation half-lives in vivo, Biochim. Biophys. Acta. 1991; 1066:29–36.

Drummond D C, Meyer O, Hong K, Kirpotin D B and Papahadjopoulos D: Pharmacol. Rev. 1999; 51:691–744.

Dobereiner H G, Kas J, Noppl D, Sprenger I and Sackmann E: *Biophys. J* 1993; 65:1396–140.

Gabizon A and Papahadjopoulos D: Liposome formulations with prolonged circulation time in blood and enhanced uptake by tumors, Proc. Natl. Acad. Sci. (Wash). 1988; 85: 6949–53.

Gordon K B, Tajuddin A, Guitart J, Kuzel T M, Eramo L R and Von Roenn J: Cancer. 1995; 75:2169–73.

Govindachari T R, Sathe S S, Viswanathan N, Pai B R and Srinivasan M: Chemical Constituents of *Cleistanthus Collinus, Tetrahedran.* 1969; 25:2815–21.

Julliano R L and Stamp D: Pharmacokinetics of liposome-encapsulated anti-tumor drugs, Biochem. Pharm. 1978; 27:21–27.

Lasic D D: Liposomes: From Physics to Applications, Amsterdam, Elsvier, 1993.

Lasic D D and Martin F: eds. Stealth Liposomes, CRC, Boca Raton, Fla., 1995

Lasic D D and Paphadjopoulos D: Medical Applications of Liposomes, Amsterdam, Elsevier, 1998.

Madden T D, Harrigan P R, Tai L C L, Bally M B, Mayer L D, Redelmeier T E, Loughrey H C, Tilcock C P S, Reinish L W and Cullis P R: The accumulation of drugs within large unilamellar vesicles exhibiting a proton gradient: a survey, Chem. Phys. Lipids. 1990; 53:37–46.

Olson F, Mayhew E, Maslow, Rustum Y and Szoka F: Characterization, toxicity and therapeutic efficacy of adriamycin entrapped in liposomes, Europ. J. Cancer. Clin. Oncol. 1982; 18:167–76.

Olson F, Hunt C, Szoka F C: Preparation of liposomes of defined size distribution by extrusion through polycarbonate membrane, BioChim. Biophys. Acta. 1979; 557: 9–23.

Rahman A, Kessler A, More N, Skies B, Rowden G, Wooley P and Schein P S: Liposomal protection of adriamycin induced cardiotoxicity in mice, Cancer Res. 1982; 40:1532–37

Sharma A, Mayhew E, Bolcsak L, Cavanaugh C and Harmon P: Activity of paclitaxel liposome formulations against human ovarian tumor xenografts, Int J Cancer. 1997; 71:103–107.

Sharma A, Sharma U S and Straubinger R M: Paclitaxel-liposomes for intracavitary therapy of intraperitoneal P388 leukemia, Cancer Lett. 1996; 107: 265–272.

Suffness M: (Ed.) Taxol, Science and Applications, Chapter 9, CRC, 1995.

William S S, Alosco T R, Mayhew E, Lasic D D, Martin F J and Bankert R B: Arrest of human lung tumor xenograft growth in severe combined immunodeficient mice using doxorubicin encapsulated in sterically stabilized liposomes, Cancer Res. 1993; 53:3964–67.

Woodle M C, Allen T M, Mayhew E and Uster P S: In vivo efficacy of vincristine entrapped in long-circulating liposomes, Proc. Am. Assoc. Cancer Res. 1992; 33:446.

Aoki H, Shirase Y, Kato J, and Watanabe Y: Emulsion stabilizing properties of soy protein isolates mixed with sodium caseinates. J. Food Sci. 1984; 49: 212–216.

Britten M, and Giroux H J: Coalescence index of protein-stabilized emulsions, J. Food Sci. 1991; 56: 792–795.

Charalambous G, and Doxastakis G: Foods Emulsifiers: Chemistry, Technology, Functional Properties and Applications. 1989; Elsevier, Amsterdam.

Dalgleish D G: Food Emulsions. In Emulsions and Emulsion Stability, J. Sjoblorn (Ed.). 1996; pp. 321–429; Marcel Dekker, New York.

Damodaran S: Amino acids, peptides and proteins, in Food Chemistry, 3rd Ed, Fennema, O. R, Ed, 1996; Marcel Dekker, New York. 321.

Das K P, and Kinsella J E: Stability of food emulsions: Physicochemical role of protein and nonprotein emulsifiers. Adv Food Nutr Res. 1990; 34: 81–201.

Demetriades K, and McClements D: Influence of pH and heating on physiochemical properties of whey protein stabilized emulsions containing a nonionic surfactant. J. Agric. Food Chem. 1998; 46: 3936–3942.

Demetriades K, and McClements D: Flocculation of whey protein stabilized emulsions as influenced by dextran sulfate and electrolyte. J. Food Sci. 1999: 64; 206–210.

Demetriades K, Coupland J, and McClements D: Physiochemical properties of whey proetein stabilized emulsions as affected by heating and ionic strength. J. Food Sci. 1997; 62: 462–467.

Dickinson E: Food emulsions and foams. Interfaces, ineractions and stability. 1999; Paston Prepress Ltd, Beccles, Suffolk.

Dickinson E, Owusu R K, and Williams A: Orthokinetic destabilization of protein stabilized emulsion by a water-soluble surfactant. Journal Chem. Soc. Faraday T. 1993; 89: 865–866.

Dickinson E, and Stainsby G: Colloids in Foods, 1982; Applied Science Publishers, London.

Dickinson E, and Williams A: Orthokinetic coalescence of protein-stabilized emulsions. Colloids and Surfaces A. 1994; 88: 317–320

Dickinson E: Introduction to Food Colloids, 1992; Oxford University Press, Oxford.

Dukhin S, and Sjoblorn J: Kinetics of Brownian and gravitational coagulation in delute emulsions, in emulsions and emulsion stability, Sjoblorn, J, Ed, 1996; Marcel Dekker, New York.

Eliel E L: Stereochemistry of Car-bon Compounds 1962; McGraw-Hill. New York

Fisher L R, and Parker N S: How do food emulsion stabilizers work. CSIRO Food Research Quarterly, 1985; 45: 33.

Haque Z, and Kinsella J: Emulsifying properties of Food Proteins: Bovine Serum Albumin. J. Food Sci. 1988; 53: 416–420.

Hasenhuettl G L, and Hartel R W: Overview of food emulsifiers, in Foods Emulsifiers and their applications. Eds, 1997; Chapman and Hall, New York.

Hasenhuettl G L, and Hartel R W: Eds, Food Emulsifiers and their applications. 1997; Chapman and Hall, New York.

Hunt J A, and Dalgleish D G: Heat Stability of oil-in-water emulsions containing milk proteins: Effect of ionic strength and pH. J. Food Sci. 1995; 60: 1120–1123.

Hunter R J: Foundations of Colloid Science, Vol. 1, 1986; Oxford University Press, Oxford.

Israelachvili J N: Intermolecular and Surface Forces. 1992; Academic Press, London.

Jost R, Baechler R, and Masson G: Heat gelation of oil-in-water emulsions stabilized by whey protein. J. Food Sci. 1986; 51; 440–444.

Krog J N: Food Emulsifiers and their chemical and physical properties. 1990; pp 128. Grindstet Products, Brabrand, Denmark.

Mangino M E: Protein ineractions in emulsions; protein-lipid interactions, In: Hettiarachchy N, Ziegler G, editors. Protein functionality in food systems. New York, N.Y.: 1994; Marcel Dekker, Inc. pp. 53–62.

Mayer L D, Tai L C L and Ko D S C (1989) Influence of vesicle size, lipid composition and drug-to-lipid ratio on the biological activity of liposomal doxorubicin in mice. Cancer Res 49: 5922–5930.

Pearce K M and Kinsella J E: Emulsifying Properties of Proteins: Evaluation of a Turbimetric technique. J. Agric. Food Chem. 1978; 26: 716–723.

Phillips L G, Whitehead D M and Kinsella J E: Structure-function Properties of Food Proteins. Academic Press, 1994; San Diego, Calif.

Sherman P: A critique of some methods proposed for evaluating the emulsifying capacity and emulsion stabilizing performance of vegetable proteins. Ital. J. Food Sci. 1995; 1: 3–10.

Smith A L and Mitchell D P: The centrifuge in the study of emulsion stability, in Theory and Practice of Emulsion Technology, Smith, A. L, Ed, Academic Press, 1976; London, chap. 4.

Tomberg E, and Hermannson A M: Functional characteristics of protein stabilized emulsions. Effect of processing. J. Food Sci. 1977; 42: 468–75.

Tornberg E, Olsson A, and Persson K: The structural and interfacial properties of food proteins in relation to their function in emulsions. 1990; pp. 254. Swedish Meat Research Institute, Kavlinge, Sweden.

van Nieuwenhuyzen W, and Szuhaj B F: Effects of lecithins and proteins on the stability of emulsions. Fett/Lipid. 1998; 100: 282–291.

Wedzicha B L: Distribution of low-molecular weight food additives in dispered systems, in Advancesin Food Emulsions, Dickinston, E. and Stainsby, G, 1 Ed, 1988; Elsevier, London, chapter 10.

Wedzicha B L, Zeb A, and Ahmed S: Reactivity of food preservatives in dispersed systems, in Food Polymers, Gels and Colloids, Dickinson, E, Royal Society of Chemistry, 1991; Cambridge, pp 180.

Working P K and Dayan A D (1996) Pharmacological-toxicological expert report. CAELYX (Stealth liposomal doxorubicin HCl). Human Exp Toxicol 15: 752–785.

Working P K, Newman M S, Carter J L, Kerl R E and Kiorpes A L (1994a) Comparative target organ toxicity of free and liposome-encapsulated doxorubicin in rats. Toxicologist 14: 217.

Working P K, Newman M S, Huang S K, Mayhew E, Vaage J and Lasic D D (1994b) Pharmacokinetics, biodistribution and therapeutic efficacy of doxorubicin encapsulated in Stealth liposomes (DOXIL). J Lipo Res 4: 667–687.

Working P K, Newman M S, Sullivan T and Yarrington J (1999) Reduction of the Cardiotoxicity of Doxorubicin in Rabbits and Dogs by Encapsulation in Long-Circulating, Pegylated Liposomes; Pharm Exp Ther 289, 1128–1133.

Yost R A, and Kinsella J E: Microstructure of whet protein isolate gels containing emulsified butterfat droplets. J. Food Sci. 1992; 57: 892–897.

What is claimed is:

1. A method of preparing protein-stabilized liposome nanoparticles containing at least one lipophilic pharmaceutical agent, the method comprising:
   (a) preparing an oil-in-water emulsion by a process comprising
      i) preparing an organic solution comprising one or more phospholipids;
      ii) mixing the at least one lipophilic pharmaceutical agent into said organic solution;
      iii) infusing said organic mixture into an aqueous solution comprising an emulsion-forming protein, wherein said emulsion-forming protein comprises from about 0.1% to about 20% (w/v) of the aqueous solution, to form a the oil-in-water emulsion; and
   (b) removing organic solvent from said emulsion to form the protein-stabilized liposome nanoparticles, wherein said liposome nanoparticles have sizes below 400 nm and said emulsion-forming protein adsorbed onto their surface.

2. The method of claim 1, wherein the organic solution further includes cholesterol.

3. The method of claim 1, wherein the organic solution further includes a PEG-phospholipid.

4. The method of claim 3, wherein said PEG-phospholipid comprises poly(ethylene glycol)-derivatized distearoylphosphatidylethanolamine (PEG-DSPE) and/or poly(ethylene glycol)-derivatized ceramides (PEG-CER).

5. The method of claim 1, wherein the lipophilic pharmaceutical agent is further identified as a substantially water insoluble pharmaceutical agent.

6. The method of claim 1, wherein the phospholipid and lipophilic pharmaceutical agent are included in the organic solution at a ratio ranging from about 0.01:25 to about 1:10 drug:lipid (w/w).

7. The method of claim 1 wherein said emulsion forming protein comprises an albumin, immunoglobulin, casein, insulin, hemoglobin, lysozyme, immunoglobulin, $\alpha$-2-macroglobulin, fibronectin, vitronectin, fibrinogen, or enzyme.

8. The method of claim 7, wherein the emulsion forming protein is an albumin.

9. The method of claim 1, wherein said aqueous solution is at a pH of between about 6.0 and 7.6.

10. The method of claim 1, wherein said emulsion-forming protein comprises from about 1% to about 10% (w/v) of the aqueous solution.

11. The method of claim 1, wherein the emulsion is formed by steps that comprise:
   (a) agitating said mixture at between about 1000 and about 24,000 revolutions per minute; and
   (b) subjecting the agitated mixture to high pressure microfluidization or homogenization at 5,000 to 30,000 PSI.

12. The method of claim 11, wherein the emulsion is formed by steps that comprise:
   (a) agitating said mixture at between about 3000 and about 10,000 revolutions per minute; and (b) subjecting the agitated mixture to high pressure microfluidization or homogenization at 10,000 to 30,000 PSI.

13. The method of claim 11, wherein the mixture is agitated using a homogenizer.

14. The method of claim 13, wherein the mixture is agitated using a rotary homogenizer.

15. The method of claim 1, wherein the lipid formulation is filtered.

16. The method of claim 15, wherein the lipid formulation is filtered through a 0.20 or 0.22 micron filter.

17. The method of claim 1, wherein the lipid formulation is lyophilized to provide a powder suitable for reconstitution in an aqueous suspension.

18. The method of claim 17, wherein the lipid formulation is lyophilized in the presence of one or more cryoprotectants.

19. The method of claim 18 wherein the cryoprotectant is sucrose, mannitol or trehalose.

20. The method of claim 1 wherein the pharmaceutical agent comprises a cardiovascular drug, respiratory drug, sympathomimetic drug, cholinomimetic drug, adrenergic or adrenergic neuron blocking drug, analgesic/antipyretic, anesthetic, antiasthamatic, antibiotic, antidepressant, antidiabetic, antifungal agent, antihypertensive agent, anti-inflammatory, antineoplastic, antianxiety agent, immunosuppressive agent, antimigraine agent, sedatives/hypnotic, antianginal agent, antipsychotic agent, antimanic agent, antiarrhythmic, antiarthritic agent, antigout agent, anticoagulant, thrombolytic agent, antifibrinolytic agent, hemorheologic agent, antiplatelet agent, anticonvulsant, antiparkinson agent, antihistamine/antipruritic, agent useful for calcium regulation, antibacterial agent, antiviral agent, antimicrobial, anti-infective, bronchodialator, hormone, hypoglycemic agent, hypolipidemic agent, protein, nucleic acid, agent useful for erythropoiesis stimulation, antiulcer/antireflux agent, antinauseant/antiemetic, oil-soluble vitamin, mitotane, visadine, halonitrosourea, anthrocycline or ellipticine.

21. The method of claim 20, wherein the pharmaceutical agent is Proscillaridin-A, oleandrin, digitoxin, digoxin, odoroside-A, colchicine, colchicine derivatives, ara-C derivatives, diphyllin, justicidin-A, diphyllin derivatives, cleistanthin A, chloroquine, amphotericin B, paclitaxel, docetaxel, cyclosporine, camptothecin, 7-ethyl-10-hydroxy-camptothecin, 10-hydroxy-camptothecin, a camptothecin derivative, podophyllotoxin, podophyllotoxin derivatives, vinblastine, vincristine, dihydroartemisinin, mitoxantrone, amphotericin B, epothilone-A, epothilone-B, epothilone-C, epothilone-D, an epothilone derivative, a benz[c]-phenanthridine alkaloid derivative, a chelerythrine alkaloid derivative or cisplatin.

22. The method of claim 1, wherein said one or more phospholipids comprise one or more of hydrogenated soy phosphatidylcholine (HSPC), egg phosphatidylcholine (EPC), phosphatidylethanolamine (PE), phosphatidylglycerol (PG), phosphatidylinsitol (PI), monosialogangolioside, spingomyelin (SPM), distearoylphosphatidylcholine (DSPC), dimyristoylphosphatidylcholine (DMPC), or dimyristoylphosphatidylglycerol (DMPG).

23. The method of claim 1, wherein the ratio of pharmaceutical agent to lipid-protein ranges from about 0.0005 to about 1 (w/w).

24. The method of claim 23, wherein the ratio of pharmaceutical agent to lipid-protein ranges from about 0.0005 to about 0.5 (w/w).

25. The method of claim 24, wherein the ratio of pharmaceutical agent to lipid-protein ranges from about 0.001 to about 0.1 (w/w).

26. The method of claim 1, wherein the lipid formulation is subjected to high shear stress to reduce particle size.

27. The method of claim 1, wherein the lipid formulation is defined further as comprising nanoparticles having size less than about 220 nm.

28. The method of claim 27, wherein the nanoparticles have a size of between about 80–160 nm.

29. The method of claim 28, wherein the nanoparticles have a size of between about 100–120 nm.

30. A protein-stabilized lipid formulation comprising protein-stabilized liposome nanoparticles and a lipophilic pharmaceutical agent, the formulation prepared by a process selected from the group of processes consisting of those processes set forth in any one of claims 1, 2–9 and 10–29.

* * * * *